United States Patent
Royster

(12) 
(10) Patent No.: US 10,876,047 B2
(45) Date of Patent: Dec. 29, 2020

(54) PHOSPHORESCENT EMITTING COMPOSITIONS

(71) Applicant: R-Display & Lighting LLC, Webster, NY (US)

(72) Inventor: Tommie L. Royster, Webster, NY (US)

( * ) Notice: Subject to any disclaimer, the term of this patent is extended or adjusted under 35 U.S.C. 154(b) by 241 days.

(21) Appl. No.: 15/381,075

(22) Filed: Dec. 15, 2016

(65) Prior Publication Data
US 2017/0174985 A1 Jun. 22, 2017

Related U.S. Application Data

(60) Provisional application No. 62/267,936, filed on Dec. 16, 2015.

(51) Int. Cl.
| | |
|---|---|
| C09K 11/06 | (2006.01) |
| H01L 51/50 | (2006.01) |
| H01L 51/00 | (2006.01) |

(52) U.S. Cl.
CPC .......... C09K 11/06 (2013.01); H01L 51/0087 (2013.01); H01L 51/5016 (2013.01); *C09K 2211/185* (2013.01)

(58) Field of Classification Search
CPC .............. C09K 11/06; C09K 2211/185; H01L 51/0087

USPC .......................................................... 556/137
See application file for complete search history.

(56) References Cited

U.S. PATENT DOCUMENTS

| | | | | |
|---|---|---|---|---|
| 7,022,422 B2* | 4/2006 | Hamada | .............. | C07F 15/0033 257/102 |
| 7,063,901 B2 | 6/2006 | Igarashi et al. | | |
| 8,017,774 B2* | 9/2011 | Kamatani | ........... | C07F 15/0033 546/2 |
| 8,734,962 B2* | 5/2014 | Adler | .................. | C07F 15/0033 428/690 |

\* cited by examiner

*Primary Examiner* — C. Melissa Koslow
(74) *Attorney, Agent, or Firm* — Hodgson Russ LLP

(57) ABSTRACT

A light emitting composition comprising a central platinum group transition metal and a bidentate ligand comprised of at least one pyridyl group with an electron donating substituent in the 4 position forming a six membered ring complex. The electron donating substituent is represented by an alkyl, aryl or amine group. The platinum group transition metal may be selected from the group consisting of platinum, palladium, iridium, rhodium, ruthenium, and osmium. Additionally, OLED devices are provided, each of the OLED devices comprising a light emitting layer that includes one of the light emitting compositions.

10 Claims, 7 Drawing Sheets

GENERIC COMPOSITIONS

GENERIC COMPOSITIONS

EXEMPLARY COMPOSITION 1

PHOSPHORESCENT EMITTING COMPOSITIONS

CROSS-REFERENCE TO RELATED PATENT APPLICATIONS

This application claims priority from U.S. Provisional Patent Application No. 62/267,936 filed Dec. 16, 2015, the disclosure of which is incorporated herein by reference.

BACKGROUND

Technical Field

Light-emitting compositions of matter. In particular, highly efficient phosphorescent emitter compositions that are useful in organic light emitting diodes.

Description of Related Art

Organic Light Emitting Diode (OLED) devices are based on strategic placement of organic thin films between electrodes (i.e. an anode and a cathode). The basic structure of an OLED device is shown in FIG. 1. Injection of holes and elections from the anode and cathode result in light emission through recombination of the holes and electrons in the light emitting layer of the "organic stack," which is the set of layers between the anode and the cathode. The organic thin films in an OLED device are typically less than 50 nanometers (nm) in thickness, resulting in low voltage operations and potential to produce low power consuming devices. These attributes are advantageous in the use of OLED devices in image display and lighting applications.

The excited states generated from hole and electron injection setup two pathways for light emission. Singlet and Triplet exciton decay yield fluorescent and phosphorescent light respectively. The ratio of Singlet to Triplet exciton formation is 1:3. Therefore, emissive layers comprised of fluorescent dopant and host materials for harvesting singlet excitons have a theoretical limit of 25% for converting excitons into light. However, phosphorescent systems can theoretically convert 100% of the excitons generated into light by harvesting Singlet excitons (after intersystem conversion) and Triplet excitons. Emissive layers are comprised of a host material and a phosphorescent dopant. Steps representing the hole/electron injection process, Triplet exciton formation and subsequent exciton decay to produce light are depicted in FIGS. 2-4.

The high efficiency of phosphorescent based OLED devices establishes a platform for manufacturing very low power consuming lighting and display applications. Based on the high efficiency, lower driving currents are required for light output, thereby establishing the potential for significant savings in power consumption. The shift from fluorescent based OLED devices to phosphorescent based devices in commercial applications has commenced. However, there are still problems that remain to be solved for broader application of phosphorescent based OLED devices to occur.

One significant problem is emitter material stability under "high current density" operations, which are required for general lighting applications. The stability of state-of-the-art phosphorescent emitters is based in part on the type of ligands that are used to form organometallic phosphorescent emitters. Currently used emitter materials known to the Applicant are comprised of bidentate cyclometalating ligands coordinated to transition metals forming a five membered ring. Two types of bonds are formed upon coordination: a charge balancing bond, typically a metal-carbon bond; and a neutral donor-acceptor or dative metal-nitrogen bond.

Calculations from at least two independent studies predict the neutral metal-nitrogen bond in cyclometalated complexes ruptures upon absorption of high energy light or thermal activation in the Triplet excited state. Although the energy associated with red and green exciton formation would have a lower probability of inducing bond rupture of the metal-nitrogen bond in cyclometalated complexes relative to blue light, under high current density operation, the potential of bond rupture increases due to several mechanisms, including thermally activated processes.

Regardless of the degradation mechanism, present OLED phosphorescent emitter materials lack the desired stability that would enable broader adaptation of these materials in lighting and image display applications. Therefore, a need remains for phosphorescent emitter materials that operate in an OLED device with high efficiency, and improved stability.

SUMMARY

The present invention meets the stated need by providing phosphorescent emitter materials that provide high efficiency and enhanced metal-ligand bond stability, thereby enabling OLED devices that have high quantum efficiency with superior lifetimes.

More particularly, in accordance with the present disclosure, a light emitting composition is provided comprising a central platinum group transition metal and a bidentate ligand comprised of at least one pyridyl group with an electron donating substituent in the 4 position forming a six membered ring complex. The electron donating substituent is represented by an alkyl, aryl or amine group. The platinum group transition metal may be selected from the group consisting of platinum, palladium, iridium, rhodium, ruthenium, and osmium. Additionally, in accordance with the present disclosure, OLED devices are provided, each of the OLED devices comprising a light emitting layer that includes one of the light emitting compositions.

BRIEF DESCRIPTION OF THE DRAWINGS

The present disclosure will be provided with reference to the following drawings, in which like numerals refer to like elements, and in which:

In FIGS. 2-4, HTL refers to a hole transporting layer, EML refers to a light emitting layer, and ETL refers to an electron transporting layer;

FIG. 3 is a schematic illustration of the triplet exciton formation process in the generation of light by an organic light emitting diode;

FIG. 4 is a schematic illustration of the subsequent exciton decay process in the generation of light by an organic light emitting diode;

Figure 6A:
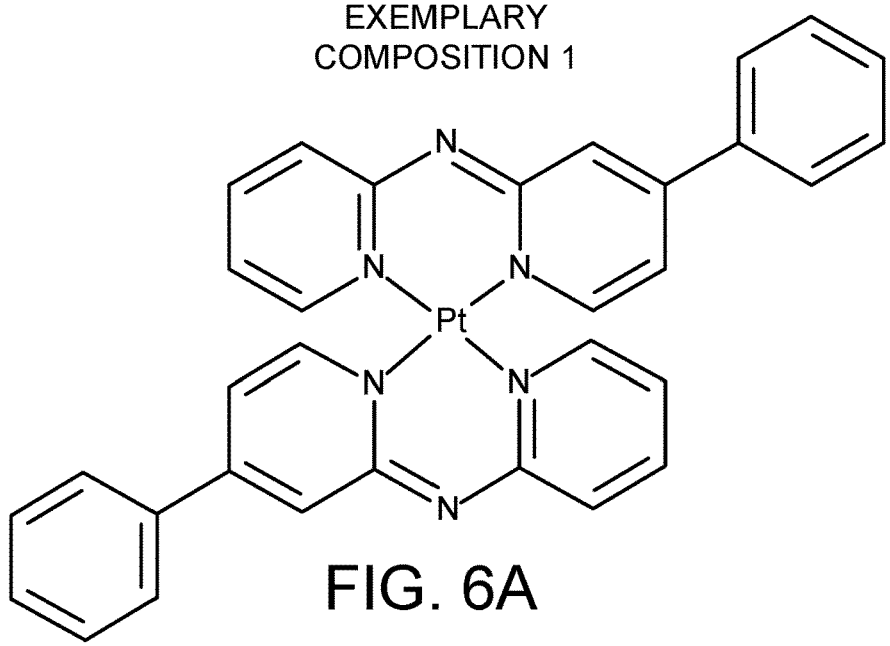
FIG. 6A is an illustration of the chemical structure of a first exemplary light-emitting composition of the present disclosure.

8A is a solution photoluminescence spectrum of exemplary emitter composition of FIG. 6A.

Figure 8A:
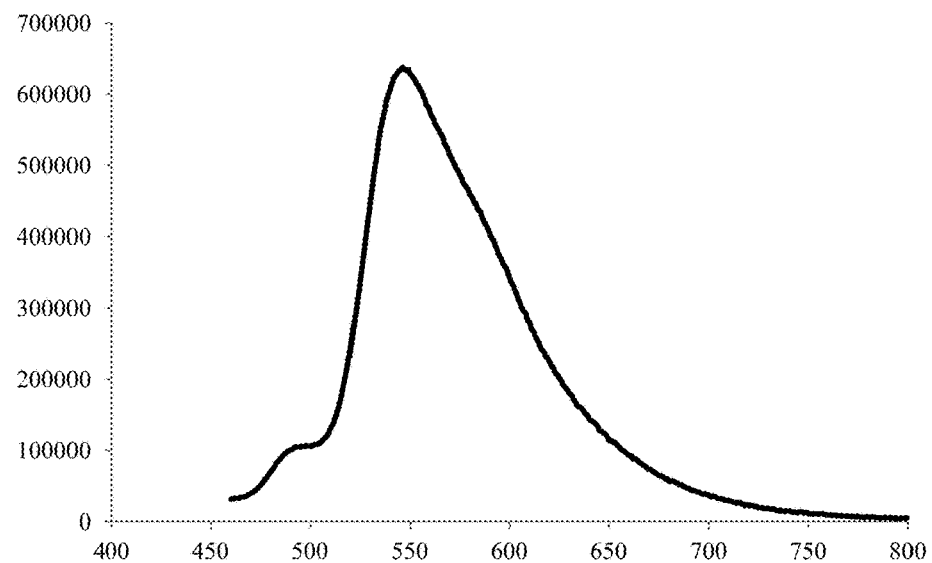
Figure 8B:
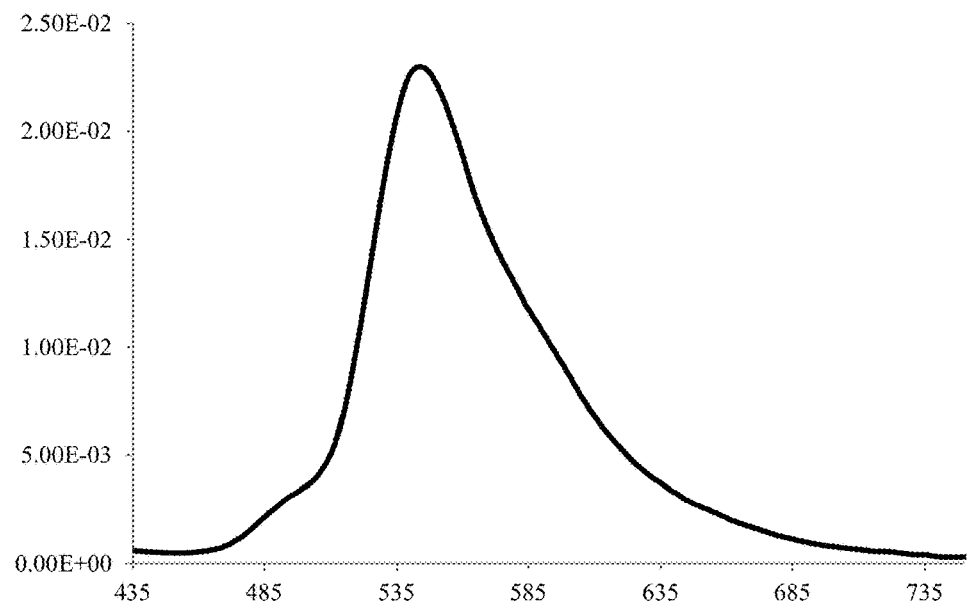

FIG. 8B is an electroluminescence spectrum of an OLED device comprised of the exemplary emitter composition of FIG. 6A.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. The drawings are to be considered as depicting exemplary embodiments of the invention, and not to be considered as limiting the invention solely to the embodiments depicted.

Figure 5A:
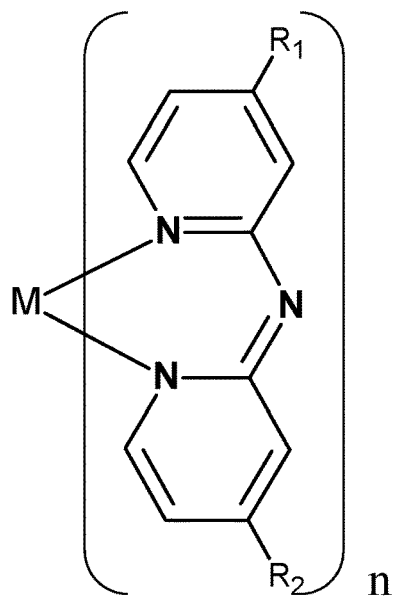
FIG. 5A is an illustration of the chemical structure of a generic light-emitting composition of the present disclosure.
Figure 5B:
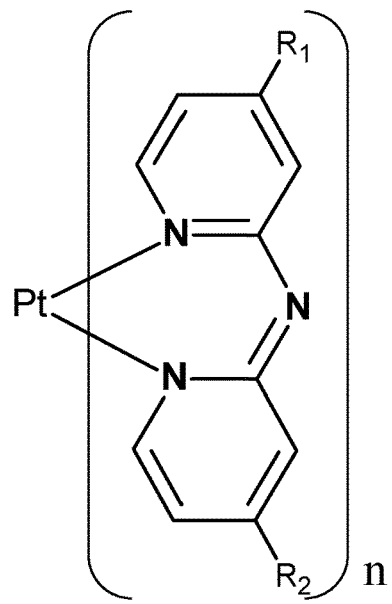
FIG. 5B is an illustration of light-emitting composition of the present disclosure comprised of platinum coordinated to a bidentate ligand class.

Through a combination of computational, synthetic and photoluminescence studies, the Applicant has discovered a new class of phosphorescent emitter material compositions that provide high efficiency and enhanced metal-ligand bond stability through unique molecular and electronic structures. General structures of the new class of compositions are shown in FIG. 5A. The structure of the "generic composition" includes a central platinum group transition metal and a bidentate ligand comprised of at least one pyridyl group with an electron donating substituent in the 4 position forming a six membered ring complex. The electron donating substituent is represented by an alkyl, aryl or amine group. In various embodiments, n may be equal to 1, 2, or 3. The Platinum Group Transition Metal may be selected from platinum (see FIG. 5B), palladium, iridium, rhodium, ruthenium, and osmium.

Figure 6B:
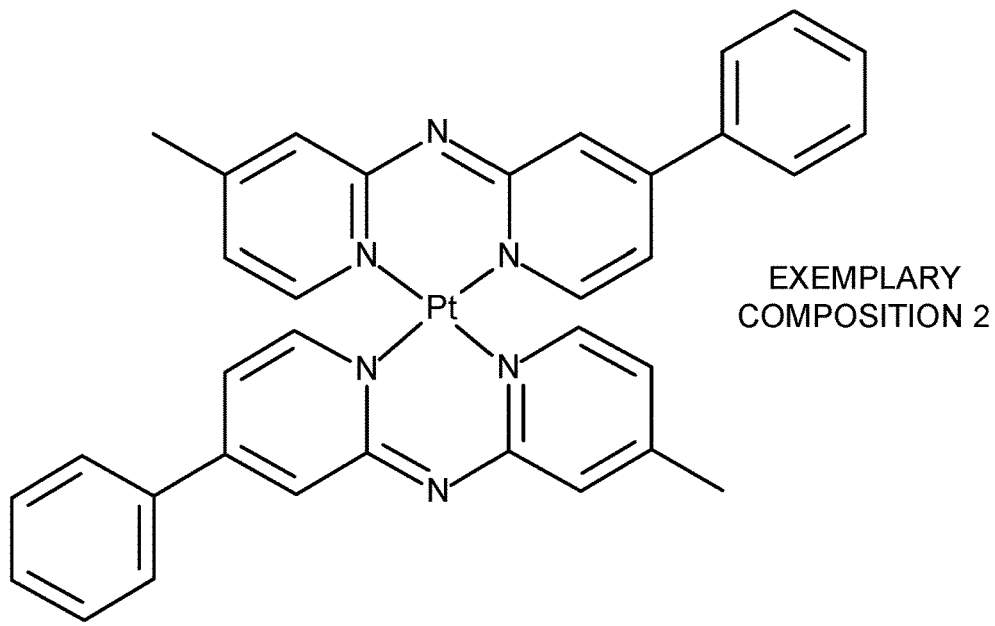
FIG. 6B is an illustration of the chemical structure of a second exemplary light-emitting composition of the present disclosure.

In various embodiments of the instant compositions, $R_1$ and $R_2$ may be selected independently of each other. In certain embodiments, $R_1$ and $R_2$ may be selected from hydrogen, an alkyl group, an aryl group (e.g., a phenyl group) or an amine group. In an example, $R_1$ is a phenyl group. By way of illustration, and not limitation, Exemplary Composition 1 and Exemplary Composition 2 are shown in FIGS. 6A and 6B.

Figure 1:
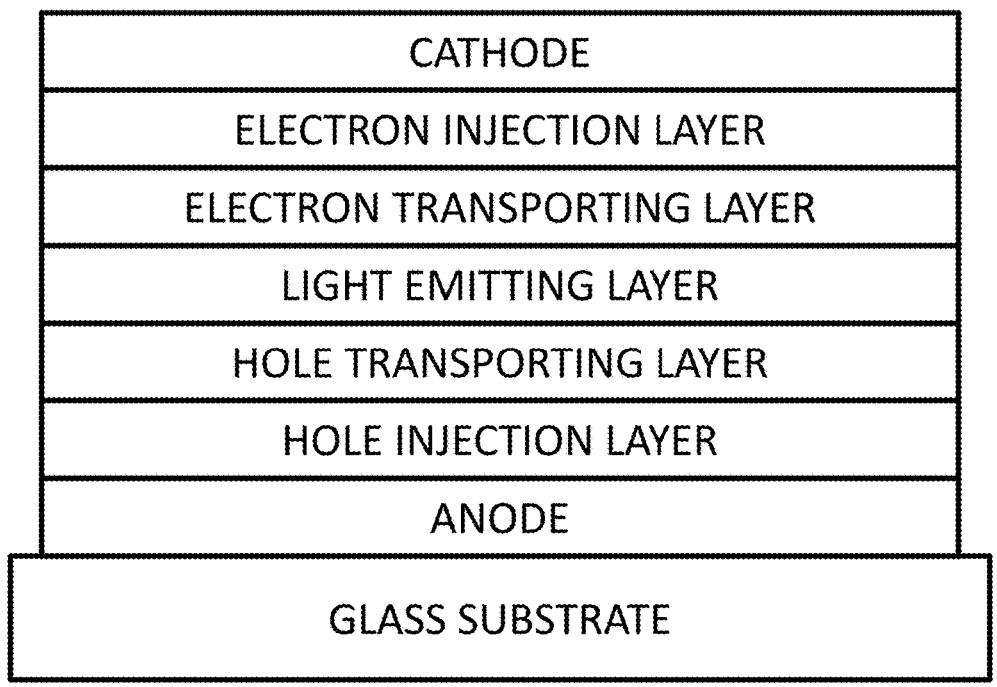
FIG. 1 is a schematic illustration of the layered structure of an organic light emitting diode.
Figure 2:
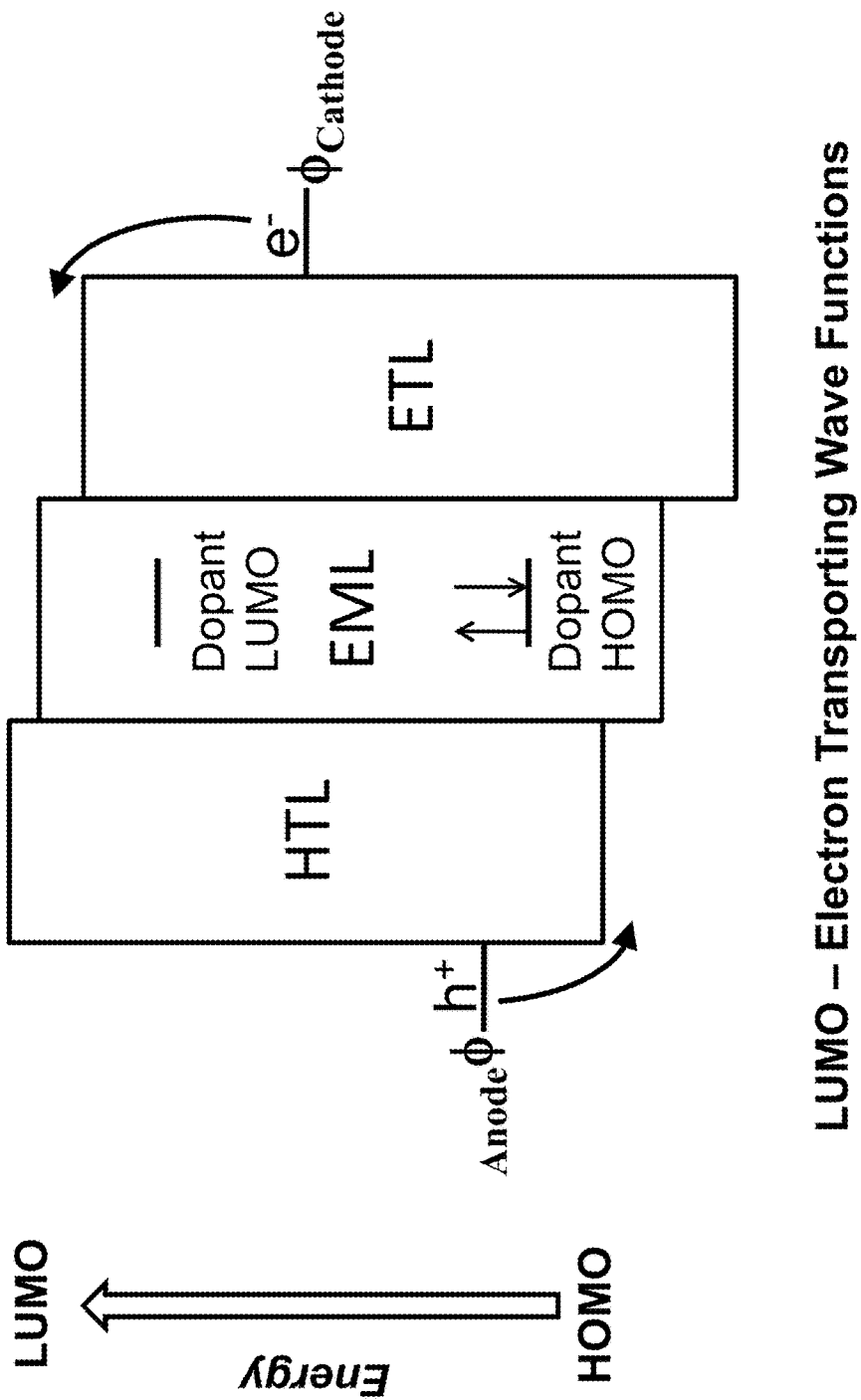
FIG. 2 is a schematic illustration of the hole/electron injection process in the generation of light by an organic light emitting diode.
Figure 3:
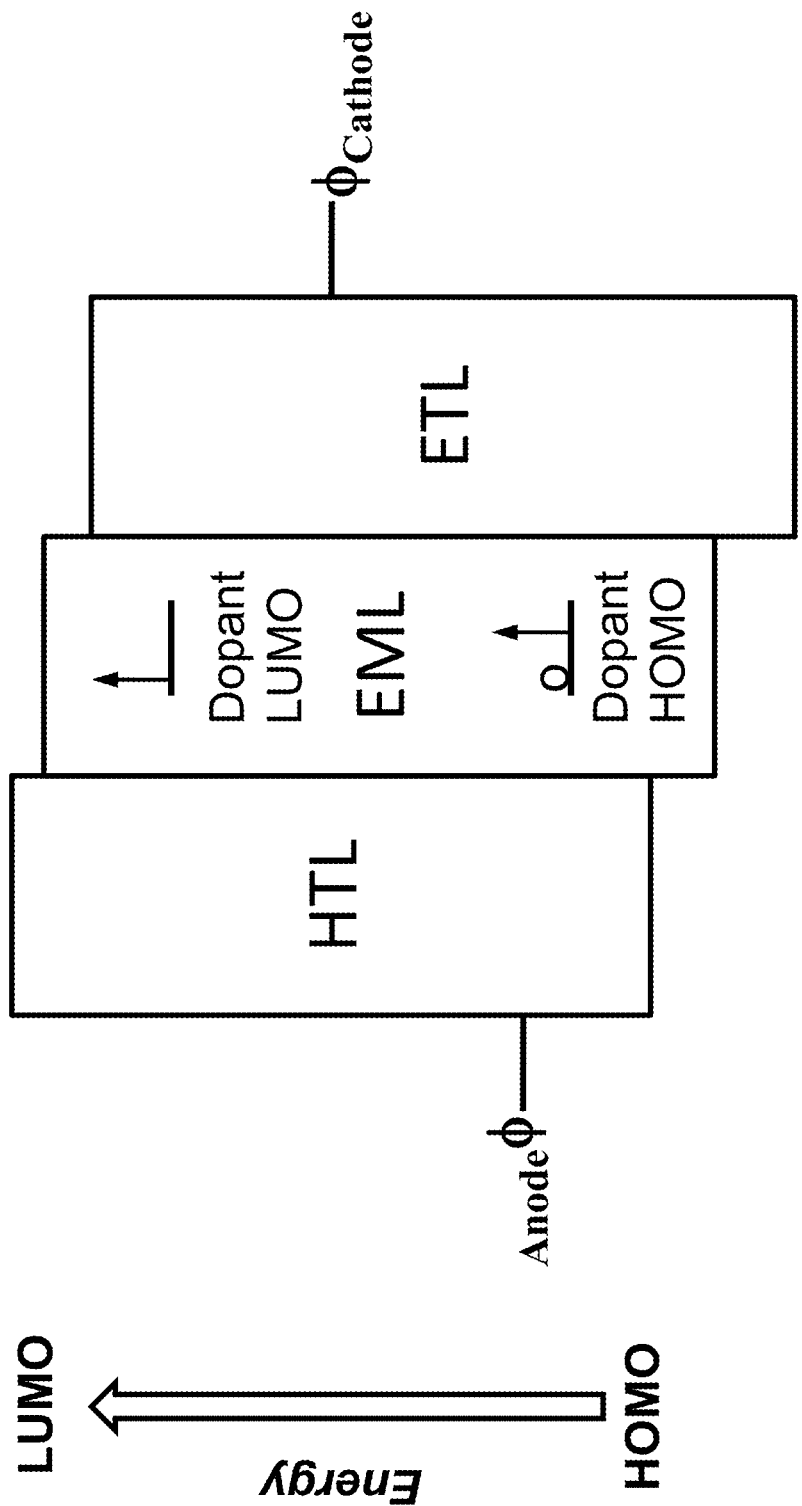
Figure 4:
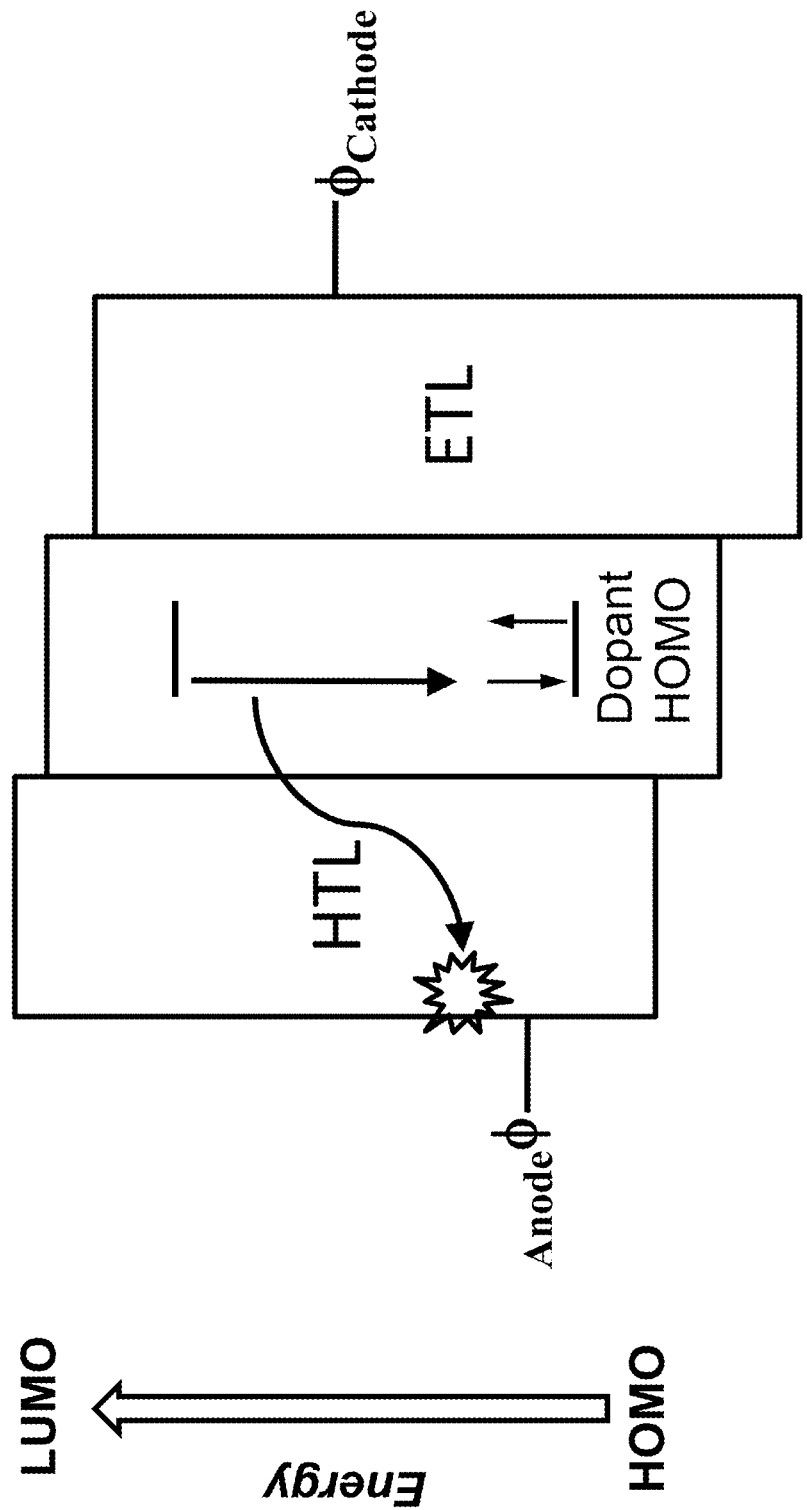

Without confinement to one specific theory, it is believed that advantageously, enhanced metal-ligand bond stability of the new compositions will lead to improved operational stability of OLED devices when used within the device light emitting layer. Support of enhanced metal-ligand stability has been indicated by Density Functional Theory (DFT) calculations of the metal-ligand bond enthalpy of dissociation for new compositions. This represents the energy required to cleave the metal-ligand bond. Higher bond dissociation energies indicate enhanced bond stability. As indicated in FIGS. 1-3, there are several steps in the process. In computational studies, the specific energy states associated with each step were considered for the bond dissociation energy calculations of various embodiments of the instant compositions using computational software tools provided by Schrödinger, LLC of Cambridge, Mass., USA. Results were obtained using the Schrödinger Materials Science Suite (MSS) (Version 1.4). Optimization of the geometries and calculations of atomic charges and ligand dissociation energies were carried out using the Jaguar Density Functional Theory (DFT) package (Version 8.4)2 using the M063 and the B3LYP4,5 hybrid density functionals.

Certain embodiments of the invention, which use strategic substitution of the heterocyclic pyridyl group, establish very high phosphorescence quantum efficiency compared to complexes with unsubstituted simple diaryl-amine ligands, such as dipyridylamine. The complex $Pt(dpa)_2$ (dpa=dipyridylamine) was prepared and used as a reference for photoluminescence quantum efficiency measurements. U.S. Pat. No. 7,063,901, the disclosure of which is incorporated herein by reference, discloses a general structure of a ligand with simple unsubstituted heterocyclic rings coordinated to a transition metal.

Figure 7:
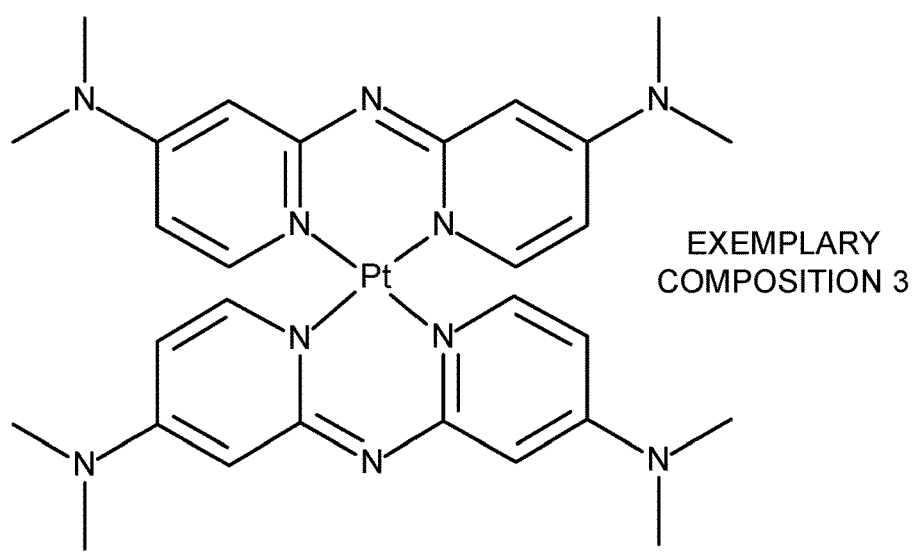
FIG. 7 is an illustration of the chemical structure of an alternative third, light-emitting composition of the present disclosure.

In certain embodiments, the instant emitter compositions are established through deprotonation of the coordinated diaryl-amine ligands. The resulting negative charge on the chelating ligand is delocalized between the bonding nitrogen atoms. Stabilization of the metal-ligand bonds is enhanced through the charge delocalization. To the best of the Applicant's knowledge, the ligands used for Exemplary Compositions 1-3 (FIGS. 6A, 6B, and 7) have not been disclosed previously for transition metal complexes.

EXAMPLES

Example 1

Method of Ligand Preparation
(N-2-Pyridyl(4-phenyl-2-pyridyl)amine)

Ligand synthesis was based on known reaction processes, such as is disclosed in U.S. Pat. No. 6,661,023, the disclosure of which is incoporated herin by reference. Provided as an example, 35 mmol of 2-amino-4-phenylpyridine and 35 mmol of 2-chloro-pyridine was introduced with 49 mmol of sodium tert-butoxide, a palladium (II) catalyst (1.4 mmol), bis(2-diphenylphosphinophenyl)ether (1.3 mmol) and 80 mL of nitrogen sparged Toluene. The reaction mixture was heated at 105° C. for 36 h under nitrogen. The reaction mixture was then diluted with ether and THF and washed with water. After passing through a pad of celite to remove insoluble particles, the organic layer was dried over $MgSO_4$ and then passed through a plug of $SiO_2$ gel using the solvent mixture $CH_2CL_2:CH_3CN$ (90:10) as the eluent. The product was isolated upon removal of solvent. After characterization, additional purification was carried out to achieve 98% purity.

Example 1

Method of Platinum Complex Preparation

In a general reaction, 3 mmol of the Pt complex $K_2PtCl_4$ was weighed out and transferred to a reaction flask. High purity water (8 mL) was then added to the flask and the solution stirred to dissolve the Pt salt. While stirring, 40 mL of 2-ethoxyethanol was added followed by the addition of the solid diaryl-amine ligand (6 mmol). An additional 5 mL of the solvent was used to rinse down any remaining ligand.

After purging with nitrogen, the flask was sealed with a Rodavise cap (a condenser with a nitrogen bubbler may also be used).

The reaction mixture was then heated in an oil bath at 75-80° C. After 24-40 hours, the heat was removed and the reaction flask allowed to cool to room temperature. The solvent was removed using a rotary evaporator. To the solid product mixture, 50 mL of acetone was added followed by 50 mL of $H_2O$. A slight excess of KOH dissolved in 20 mL of water was added to promote deprotonation. After stirring at room temperature for at least 1 hour, the solvent was reduced and additional $H_2O$ was added to dissolve the salts and promote product precipitation. The product was collected by filtering using a medium porosity fritted funnel and allowed to air dry. (Alternatively, drying in vacuo would be acceptable.) Characterization of the product was carried out primarily using mass spectroscopy and elemental analysis.

Example 2

Photoluminescence Measurements

Toluene solutions of Exemplary Compositions 1 and 2 (FIGS. 6 and 7) and the reference emitter Pt(dpa)$_2$ were sparged with nitrogen prior to photoluminescence measurements. Absorption spectra were first obtained to determine the best excitation wavelength. A comparison of the measured solution quantum efficiencies from the photoluminescence measurements are provided in TABLE 3.

TABLE 3

| Quantum Efficiency (QE) Data | |
| --- | --- |
| Material | QE |
| Inv. 1 | >0.62 |
| Pt(dpa)$_2$ | <0.17 |

The observed significant increase in phosphorescence QE for Exemplary Compositions 1 over the reference base structure clearly demonstrate the influence of strategic substitution. The photoluminescence spectra of Exemplary Composition 1 is shown in FIG. 8A.

Example 3

Device Fabrication

A glass substrate coated with about a 21.5 nm layer of indium-tin oxide (ITO), as the anode, was sequentially washed in a commercial detergent, rinsed in deionized water, rinsed with acetone, and exposed to an oxygen-plasma for about 1 min. Over the ITO, a 10 nm thick hole-injecting layer (HIL), LG-101, manufactured and sold by LG Chem Corporation of Seoul, South Korea, was vapor deposited. Next, a layer of a Hole Transporting Material, N,N'-Di(1-naphthyl)-N,N'-diphenyl-(1,1'-biphenyl)-4,4'-diamine (NPB) was deposited to a thickness of 30 nm. A 40 nm light-emitting layer (LEL) comprising a carbazole host and Exemplary Composition 1 (16%) was then deposited. An electron-transporting layer corresponding to 550 nm of 2,2',2"-(1,3,5-Benzinetriyl)-tris(1-phenyl-1-H-benzimidazole) (TPBi) was vacuum-deposited followed by 0.5 nm of the electron-injecting layer lithium fluoride. Finally, 150 nm layer of aluminum was deposited to form a cathode layer.

The electroluminescence spectrum recorded from the device is shown in FIG. 8B. The spectral features were consistent with the photoluminescence spectrum. The luminous yield for the non-optimized device was very high for the recorded CIE coordinates (TABLE 4).

TABLE 4

| OLED Device Data | |
| --- | --- |
| Luminous Yield cd/A | CIEx, y |
| 68 | 0.385, 0.567 |

It is therefore apparent that there has been provided, in accordance with the present disclosure, phosphorescent emitting compositions, and light emitting diodes comprised of such compositions. Having thus described the basic concept of the invention, it will be apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention.

I claim:

1. A light emitting composition comprised of a central platinum group transition metal (M) selected from platinum, palladium, iridium, rhodium, ruthenium, and osmium and a bidentate ligand comprised of at least one pyridyl group including an electron donating substituent in the 4 position and forming a six membered ring complex, wherein the composition has the structure:

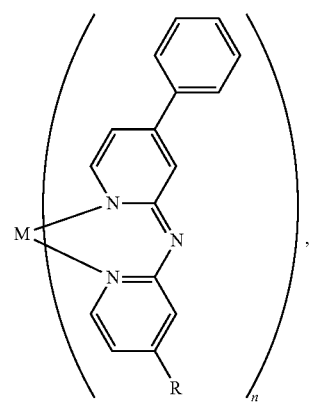

and wherein R is independently selected from an alkyl group and an aryl group, and n=1, 2, or 3.

2. The composition of claim 1, wherein the platinum group transition metal is platinum.

3. The composition of claim 2, wherein the composition has the structure:

4. The composition of claim 2, wherein the composition has the structure:

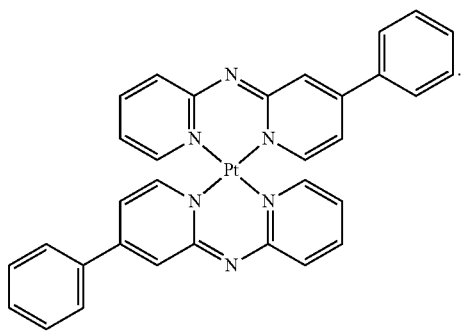

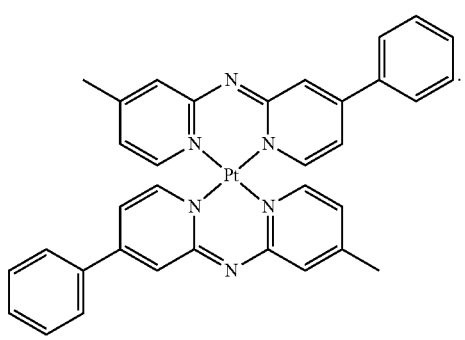

5. An OLED device comprising a light emitting layer including a light emitting composition comprised of a central platinum group transition metal (M) selected from platinum, palladium, iridium, rhodium, ruthenium, and osmium and a bidentate ligand comprised of at least one pyridyl group including an electron donating substituent in the 4 position and forming a six membered ring complex wherein the composition has the structure:

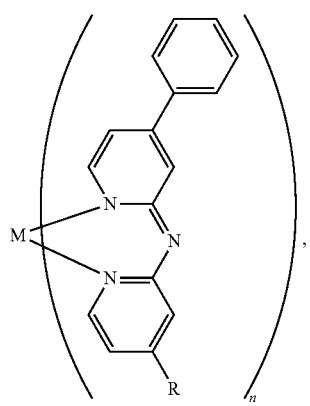

and
  wherein R is independently selected from an alkyl group and an aryl group, and
  n=1, 2, or 3.

6. The OLED device of claim 5, wherein the platinum group transition metal is platinum.

7. The OLED device of claim 6, wherein the composition has the structure:

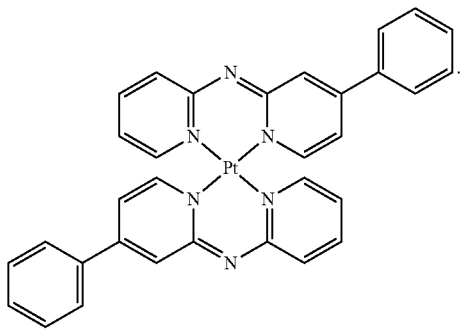

8. The OLED device of claim 6, wherein the composition has the structure:

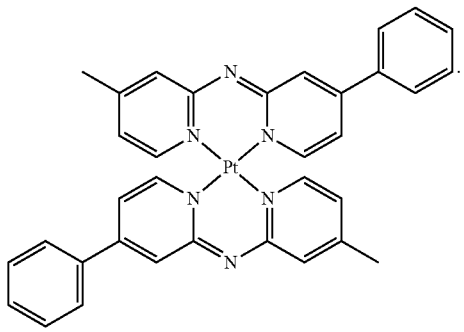

9. A light emitting composition comprised of a central platinum group transition metal and a bidentate ligand comprised of at least one pyridyl group including an electron donating substituent in the 4 position and forming a six membered ring complex, wherein the composition has the following structure:

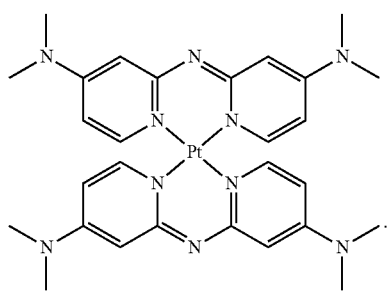

10. An OLED device comprising a light emitting layer including a light emitting composition comprised of a central platinum group transition metal and a bidentate ligand comprised of at least one pyridyl group including an electron donating substituent in the 4 position and forming a six membered ring complex wherein the composition has the structure:

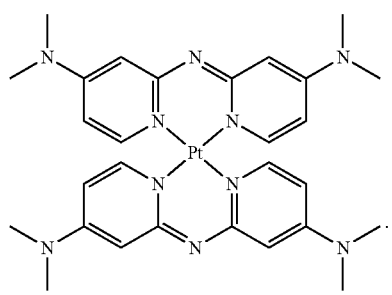
* * * * *